US00PP25192P3

(12) United States Plant Patent
Wood

(10) Patent No.: US PP25,192 P3
(45) Date of Patent: Dec. 30, 2014

(54) ***GREVILLEA* HYBRID PLANT NAMED 'TWD01'**

(50) Latin Name: ***Grevillea* hybrid**
Varietal Denomination: TWD01

(71) Applicant: Michael Wood, Bega (AU)

(72) Inventor: Michael Wood, Bega (AU)

( * ) Notice: Subject to any disclaimer, the term of this patent is extended or adjusted under 35 U.S.C. 154(b) by 168 days.

(21) Appl. No.: 13/694,093

(22) Filed: Oct. 26, 2012

(65) Prior Publication Data

US 2014/0123351 P1 May 1, 2014

(51) Int. Cl.
*A01H 5/00* (2006.01)

(52) U.S. Cl.
USPC ..... Plt./226

(58) Field of Classification Search
CPC ..... A01H 5/02; A01H 5/00; A01H 5/025; A01H 5/12
USPC ..... Plt./226, 263.1
See application file for complete search history.

(56) References Cited

PUBLICATIONS

EcoLandscape California 2013, *Grevillea juniperina* 'Molonglo' retrieved on May 29, 2014, retrieved from Internet at <http://www.ecolandscape.org/plantProfiles/Grevillea_juniperina_Molonglo.pdf> one page.*

Upov Pluto Plant Variety Database 20140523, retrieved on May 29, 2014, retrieved from Internet at <http://www.upov.int/pluto/en/index.jsp> for *Grevillea* 'TWD01', one page.*

* cited by examiner

*Primary Examiner* — June Hwu
(74) *Attorney, Agent, or Firm* — Sam McCoy

(57) ABSTRACT

'TWD01' is a distinctive variety of *Grevillea* hybrid which is characterized by a short plant height, a denser plant habit, larger leaves, and a compact red flower.

2 Drawing Sheets

Latin name of the genus and species: The Latin name of the genus and species of the novel variety disclosed herein is *Grevillea* hybrid.

Variety denomination: The inventive variety of *Grevillea* hybrid disclosed herein has been given the variety denomination 'TWD01'.

The present application claims priority from a provisional U.S. application No. 61/552,182 filed Oct. 27, 2011, which is herein incorporated by reference.

BACKGROUND OF THE INVENTION

The present invention relates to a new and distinct perennial variety of *Grevillea* hybrid, which has been given the variety denomination of 'TWD01'. Its market class is that of an ornamental plant. 'TWD01' is intended for use in landscaping and as a decorative plant.

Parentage: In 2004 a seedling occurred from open pollination between two parents, red-form *Grevillea rhyolitica* (unpatented) and *Grevillea juniperina* 'Molonglo' (unpatented). The seedling exhibited a shorter plant height, a denser habit and larger leaves when compared to either parent plant. Upon flowering, the new seedling, which was named 'TWD01', exhibited a red flower like that of parent plant *Grevillea rhyolitica*. By comparison, 'TWD01' has a shorter plant height, more compact overall habit, larger leaves and a more compact flower.

Asexual Reproduction: 'TWD01' was first propagated asexually by vegetative cuttings in the state of New South Wales, Australia in 2005 and has since been asexually propagated by micropropagation. The distinctive characteristics of the inventive 'TWD01' variety are stable from generation to generation; clones of the variety produced by asexual reproduction maintain the distinguishing characteristics of the original plant.

An application for plant breeders' rights for variety 'TWD01' has been lodged with the Australian Plant Breeders' Rights Office, and was first gazetted in 22 Dec. 2010 under Application No. 2010/281.

SUMMARY OF THE INVENTION

'TWD01' is a distinctive variety of *Grevillea* hybrid which is characterized by a short plant height, a denser plant habit (assessment of foliage at flowering), larger leaves, and a compact red flower.

BOTANICAL DESCRIPTION OF THE PLANT

Figure 1:
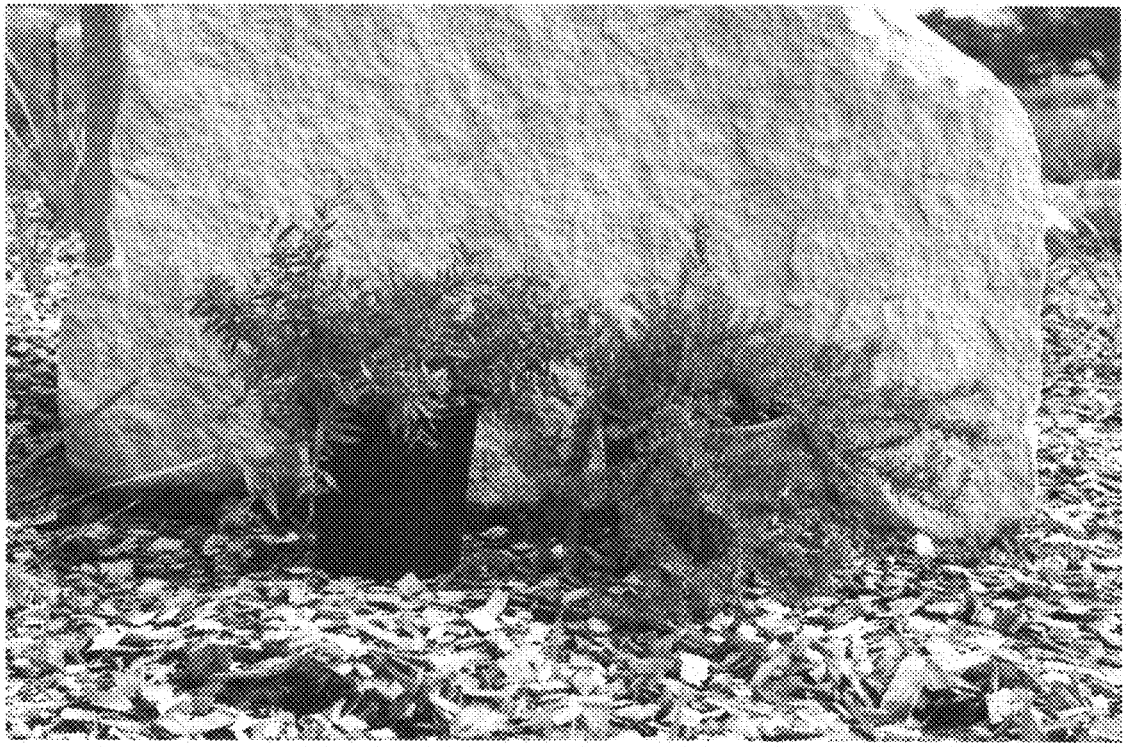
FIG. 1 shows a mature 'TWD01' plant, on left, compared to the seed parent red-form *Grevillea rhyolitica* (unpatented).
Figure 2:
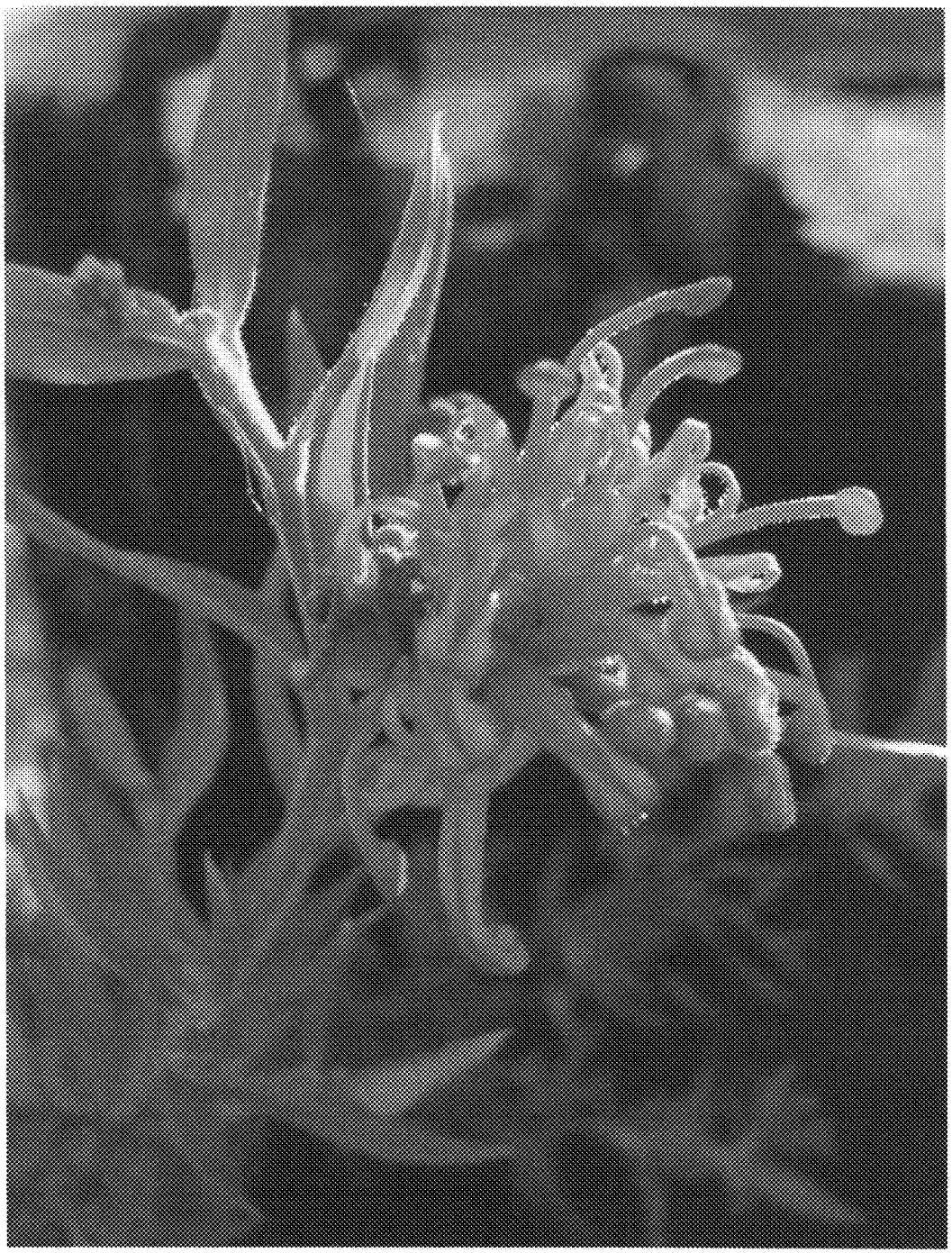
FIG. 2 shows a close up of the 'TWD01' flower.

The following is a detailed botanical description of a new and distinct variety of a *Grevillea* hybrid ornamental plant known as 'TWD01'. Plant observations were made on plants grown in New South Wales, Australia. Unless indicated otherwise, the descriptions disclosed herein are based upon observations made from mature 'TWD01' plants grown from rooted cuttings from November 2010 to August 2011 in 200 mm nursery pots filled with soilless potting media, maintained with granular slow release fertilizer and regularly watered with overhead irrigation. No pest and disease measures were taken. Observation data was recorded in August 2011.

Those skilled in the art will appreciate that certain characteristics will vary with older or, conversely, younger plants. 'TWD01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 2001 edition. Note that generic color descriptions such as 'white' do not exist in the RHS charts and the corresponding RHS colors are quoted.

'TWD01' is a perennial *Grevillea* hybrid plant which is a seedling selection from parents *Grevillea juniperina* 'red form' (unnamed and unpatented) and *Grevillea juniperina* 'Molonglo' (unpatented). After its selection, 'TWD01' was asexually propagated by vegetative cuttings. 'TWD01' is characterized by a short plant height, a denser plant habit, larger leaves, and a compact red flower. These features and other characteristics are apparent from the description provided below.

GROWTH HABIT, DIMENSIONS AND COLOR

Plant description:

*Plant habit*.—Fruticose, prostrate and dense to very dense.

*Height*.—Approximately 40 cm.

*Width*.—Approximately 80 cm.

*Bloom period*.—Spring and sporadically in fall and winter in warmer climates.

*Hardiness*.—USDA Zone 9 to 11.

*Environmental tolerances*.—Shade tolerance. Drought tolerance.

*Pest and disease susceptibility or resistance*.—In common with the species, none of note.

*Propagation*.—Propagation is accomplished using softwood cuttings. Roots well without rooting compound or hormone.

*Time to develop roots*.—2 to 4 weeks.

*Crop time*.—From six to 10 months are needed to produce a 14-centimeter container with plant in flower, starting from a rooted cutting.

Stems: Strong stems are prostate and freely-branched with more than 20 stems present. Shape is cylindrical; texture is corky; immature stems exhibit a combination of hues most closely described as a combination of greyed-purple 182B to greyed-green 194B. Mature color closest to yellow green 152D. Internode length averages 7 mm.

Leaf: Shape is elliptical; apex is acute; margin is entire. Upper surface is glabrous and lower surface is pubescent. Average length is 33.5 mm and the average width is 8.8 mm. Color of the upper surface is green corresponding to RHS 137A and the lower leaf surface is yellow-green corresponding to 146A.

Roots: Clusters of closely spaced short lateral rootlets.

Inflorescence: Umbellate inflorescences, 32 mm long and 34 mm wide on average, and borne on a short rachis, erect to semi-erect and very short with pedicels leaning away from the rachis. Rachis is approximately 14 to 18 mm long and 2 to 4 mm wide; rachis texture is smooth and pubescent; rachis color is a combination of hues most closely described as a combination of greyed-purple 182B to greyed-green 194B. Pedicels are short, approximately 5 mm long and 1 mm wide, and pubescent; pedicel color is a combination of greyed-purple 182B to greyed-green 194B. Inflorescence color is red (RHS 45A). Flower opening sequence can be described as centrifugal. Approximately 18 to 24 florets per inflorescence.

Flowers: Perianth color is red (RHS 45A); weak pubescence; perianth tube width averages 4 mm with an average length of 18.5 mm, including the style. Stigma and style color is red (RHS 45A) and has an average length of 16 mm; ovary green (RHS 137A); nectary red (RHS 45A). Pollen presenter is orange in color and its shape is flat. Pollen is white.

Fruit and Seed: Not observed.

COMPARISON OF TWD01 WITH OTHER VARIETIES OF *GREVILLEA* HYBRID

Several of *Grevillea* were initially compared to 'TWD01' but were ultimately excluded as comparators for one or more reasons. The inflorescence of 'TWD01' is umbellate whereas those of *Grevillea juniperina*×*rhyolitica* hybrid 'Ember Glow' (unpatented) are secund. The perianth, the pistil and the pollen presenter of 'TWD01' are all red (RHS 45A) whereas the perianth of 'Ember Glow' is a slightly lighter shade of red (RHS 42A) and the outer portion of the pistil, particularly at the pollen presenter, is yellow-green (RHS 153C, 1986 edition). Both 'TWD01' and 'Ember Glow' are considered to have a groundcover habit yet 'TWD01' has a mature height and spread that is approximately 50% smaller than 'Ember Glow'. *Grevillea victoriae* hybrid×*Grevillea rhyolitica* 'Lady O' (unpatented) would also be considered a groundcover form of *Grevillea* which has a similar habit' leaf size and shape and similar flower color compared to that of 'TWD01'. However, 'TWD01' has a mature height and spread that is approximately 40% smaller than that of 'Lady O'. Furthermore 'TWD01' has an umbellate inflorescence whereas 'Lady O' has an irregular inflorescence. *Grevillea* hybrid 'Gold Fever' (unpatented) is a cross is yet another groundcover *Grevillea* with a similar height and spread, leaf shape and leaf size. However, 'Gold Fever' has a greyed-yellow perianth (RHS 161C, 1986 edition) whereas the perianth of 'TWD01' is red (RHS 45A). For the reasons presented above, these varieties were excluded as the most similar variety known to the breeder.

The most similar variety known to the breeder is *Grevillea juniperina* hybrid 'New Blood' (unpatented). Both 'TWD01' and 'New Blood' have a spreading and prostrate habit with a short plant height. Both also have a flower that is approximately the same hue of red and of similar size. However, there are certain characteristics that distinguish 'TWD01'. At flowering, the foliage of 'TWD01' is less dense compared to that of 'New Blood'. 'TWD01' has a larger leaf (average length is 33.5 mm and the average width is 8.8 mm) compared to that of 'New Blood' which has an average length of 20.9 mm and width of 4.3 mm. Also the leaf of 'TWD01' is less glossy than that of 'New Blood'. The flower of both 'TWD01' and 'New Blood' are similar but 'TWD01' has branched inflorescence and a red nectary whereas 'New Blood' almost completely lacks this branching and has a white nectary.

The combination of its short plant height, a denser plant habit, larger leaves, and a compact red flower makes 'TWD01' a desirable ornamental plant suited for mass production for pot and landscape use.

That which is claimed is:

1. A new and distinct variety of *Grevillea* hybrid plant named 'TWD01', substantially as described and illustrated herein.

* * * * *